(12) United States Patent
Tamerlani et al.

(10) Patent No.: US 7,361,745 B2
(45) Date of Patent: Apr. 22, 2008

(54) PROCESS FOR THE PREPARATION OF 1-CHLORO-3,5-DI-O-ACYL-2-DEOXY-L-RIBOFURANOSIDE DERIVATIVES

(75) Inventors: Giancarlo Tamerlani, Casola di Castel di Casio (IT); Debora Bartalucci, Vinci (IT); Liana Salsini, Ripa (IT); Silvia Rapaccini, Piombino (IT)

(73) Assignee: Inalco S.p.A., Milan (IT)

( * ) Notice: Subject to any disclaimer, the term of this patent is extended or adjusted under 35 U.S.C. 154(b) by 0 days.

(21) Appl. No.: 10/578,800

(22) PCT Filed: Nov. 10, 2004

(86) PCT No.: PCT/EP2004/052900
§ 371 (c)(1), (2), (4) Date: May 9, 2006

(87) PCT Pub. No.: WO2005/044832
PCT Pub. Date: May 19, 2005

(65) Prior Publication Data
US 2007/0083041 A1   Apr. 12, 2007

(30) Foreign Application Priority Data
Nov. 10, 2004   (IT) .......................... FI2003A00288

(51) Int. Cl.
*C07G 3/00* (2006.01)
*C07H 15/00* (2006.01)
*C07H 17/00* (2006.01)
*C07D 307/02* (2006.01)

(52) U.S. Cl. .................... 536/18.5; 536/18.6; 549/475

(58) Field of Classification Search .................... None
See application file for complete search history.

(56) References Cited

OTHER PUBLICATIONS

Nagarajan, et al. Journal of Heterocyclic Chemistry 1997, 34, pp. 1581-1585.*
Mormann et al. Acta Polym. 1999, 50, 20-27.*
Fox et al. Journal of the American Chemical Society 1961, 83, 4066-70.*
Zhang et al., "Improved Synthesis of 2-Deoxy-L-Ribose", *Nucleosides & Nucleotides*, vol. 18 (11 & 12), 2357-2365 (1999).

* cited by examiner

*Primary Examiner*—Shaojia Anna Jiang
*Assistant Examiner*—Layla Bland
(74) *Attorney, Agent, or Firm*—Abelman, Frayne & Schwab

(57) ABSTRACT

Herein described is a process for the preparation of 1-chloro-3,5-di-O-acyl-2-de-oxy-L-ribofuranoside derivatives of general formula (I) useful as intermediates in processes for preparing nucleotides of the L series having antiviral activity

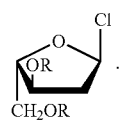

(I)

22 Claims, No Drawings

PROCESS FOR THE PREPARATION OF 1-CHLORO-3,5-DI-O-ACYL-2-DEOXY-L-RIBOFURANOSIDE DERIVATIVES

FIELD OF INVENTION

The present invention concerns a process for the industrial preparation of 1-chloro-3,5-di-O-acyl-2-deoxy-L-ribofuranoside derivatives of general formula (I) hereinafter reported, useful as precursors for the preparation of nucleosides of the L series having antiviral activity.

PRIOR ART

Nucleosides of the L series are products having a rising importance since they are always more used as antiviral agents for their high biological activity and lower toxicity compared to corresponding nucleosides of D series.

Therefore, also the derivatives 1-chloro-3,5-di-O-acyl-2-deoxy-L-ribofuranosides, as precursors of said nucleosides of L series, are very important products.

In literature, up today, methods have been described for the preparation of 1-chloro-3,5-di-O-acyl-2-deoxy-L-ribofuranoside derivatives, in particular 1-chloro-3,5-di-O-p-toluoyl-2-deoxy-L-ribofuranoside, starting from 2-deoxy-L-ribose, as can be seen in W. Zhang et al. *Nucleosides and Nucleotides* 1999, 18, 2357-2365.

This method of synthesis consists in a first step of preparation of 1-O-methyl-2-deoxy-L-ribofuranoside starting from 2-deoxy-L-ribose through treatment with a methanolic solution of hydrochloric acid for 1 hour at room temperature and subsequent neutralisation with pyridine; the obtained product is purified by chromatography on a column of silica gel. In the subsequent step the 1-O-methyl-3,5-di-O-p-toluoyl-2-deoxy-L-ribofuranoside is prepared by reacting 1-O-methyl-2-deoxy-L-ribofuranoside with p-toluoyl chloride as acylating agent using pyridine both as solvent and as base; the product is purified by chromatography on a silica gel column. Finally, the last step of the process described by W. Zhang et al. sets forth the use of ether as reaction solvent in which the hydrochloric acid is bubbled. The product precipitates directly in the reaction environment.

The method of synthesis described by W. Zhang et al. has therefore various disadvantages and it is not scalable. The main disadvantages of this method are the use of a noxious solvent as pyridine in high quantities; the use, in last step of the process, of ether that is a highly inflammable solvent; and the necessity to purify the products obtained in the first two steps of the process by chromatography on silica gel. Finally, such process uses, as starting material the 2-deoxy-L-ribose that is an expensive product and, in its turn, it is prepared with various known methods that are all disadvantageous and difficult to be industrially used as they require expensive reagents and/or dangerous products to be handled on a large scale.

Therefore, in view of the foregoing, it is deeply felt the need to have available a process for the preparation of the above said ribofuranosidic derivatives that is scalable, economically advantageous and not have the disadvantages above mentioned for the known processes.

SUMMARY OF THE INVENTION

Now the Applicant has found a new process for the preparation in high yields of 1-chloro-3,5-di-O-acyl-2-deoxy-L-ribofuranosidic derivatives of formula (I) hereinafter reported, having high purity, avoiding the use of dangerous solvents and allowing the industrial scaling up of the process.

Subject of the present invention is therefore a process for the preparation of 1-chloro-3,5-di-O-acyl-deoxy-L-ribofuranosidic derivatives of formula (I)

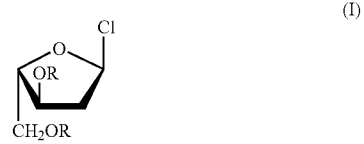

wherein R is an acyl group R'CO, in which R' is selected from the group consisting of alkyl groups C1-C6 and aryl groups C7-C13, possibly substituted with one or more substituents;

said process comprising the following steps:

i) reaction of 2-deoxy-D-galactose of formula (II) with methanol in the presence of an acid as catalyst to obtain the 1-O-methyl-2-deoxy-D-galactofuranoside of formula (III):

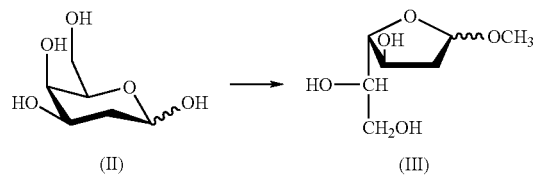

ii) oxidation of 1-O-methyl-2-deoxy-D-galactofuranoside of formula (III) coming from step i) with sodium meta periodate to obtain the corresponding aldehyde of formula (IV):

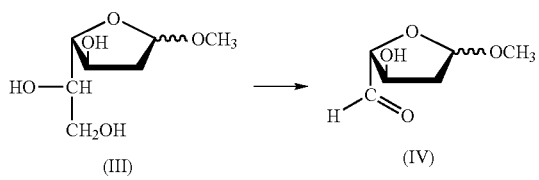

iii) reduction of the aldehyde of formula (IV) coming from step ii) with sodium borohydride to obtain the 1-O-methyl-2-deoxy-L-ribofuranoside of formula (V):

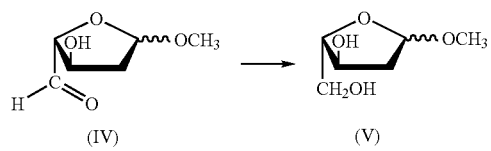

iv) acylation of O-methyl-2-deoxy-L-ribofuranose of formula (V) coming from step iii) with an acyl chloride of formula R'COCl, in presence of a tertiary amine base in an aprotic solvent to obtain the corresponding 1-O-methyl-3,5-di-O-acyl-2-deoxy-L-ribofuranoside having formula (VI):

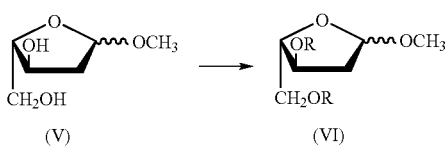

in which R' and R are defined as above;

v) chlorination of 1-O-methyl-3,5-di-O-acyl-2deoxy-L-ribofuranoside of formula (VI) coming from step iv) with gaseous hydrochloric acid at a temperature lower than 20° C. to obtain 1-chloro-3,5-di-O-acyl-2-deoxy-L-ribofuranoside of formula (I):

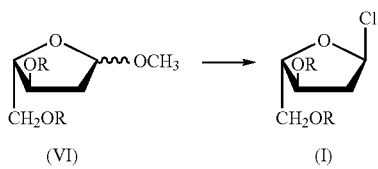

where R is defined as above.

Features and advantages of the present invention will be described in details in the following description.

DETAILED DESCRIPTION OF THE INVENTION

According to the invention "alkyl groups C1-C6" are for example methyl, ethyl and propyl groups, whereas by the expression "aryl groups C7-C13" the benzoyl group is meant for example.

The above mentioned groups may possibly have one or more substituents, chosen for example from amongst halogens, alkyl groups C1-C4, alkyloxy groups C1-C4 and nitro groups.

According to the present invention R' is preferably benzoyl, possibly substituted by a group chosen from between p-chloro and p-methyl.

The process developed by the Applicant allows the preparation of 1-chloro-3,5-di-O-acyl-2-deoxy-L-ribofuranoside derivatives (I) by a simple method, economically advantageous and easy to be scaled up. Moreover, this process allows to avoid the use of 2-deoxy-L-ribose as starting material and to overcome the disadvantages above highlighted for the known methods.

Step i) of the present process is preferably carried out with anhydrous methanol in amount ranging between 2 and 20 litres per kilogram of 2-deoxy-D-galactose; furthermore, as acid catalyst the preferred product is an acid obtained by hydrolysis of an acyl chloride, such as acetyl chloride, added in catalytic amount, for example in amount ranging between 0.01 and 0.2 litres of acyl chloride per kilogram of 2-deoxy-D-galactose.

Step i) of the present process is preferably kept under control in order to keep the inner temperature of reaction below 3° C., thus limiting the formation of the pyranoside derivative at a percentage lower than 10% in moles.

The oxidation with sodium metaperiodate in step ii) is carried out using from 1 to 1.5 moles of oxidising agent compared to the compound of formula (III) to be oxidised; the strong exothermy produced following to the addition of $NaIO_4$ can be controlled, for example, either by an external cooling, or by introducing ice directly in the reaction mixture, so as to keep the inner temperature of reaction below 10° C. In this way, any collateral reaction that can waste the product is avoided.

The reaction in step iii) of the present process is preferably carried out in water with sodium borohydride in an amount ranging between ⅓ and 1 mole of reducing agent compared to the substrate of formula (IV) to be reduced, keeping the inner temperature of reaction below 15° C. At the end of reaction, before moving to the following step, salts are eliminated from the syrup obtained after concentration; the syrup is heated and suspended in acetone, thereafter the precipitated salts are filtrated or, alternatively, the salts can be eliminated with ion exchange resins according to known procedures.

The acylation reaction in step iv) of the present process occurs in positions 3 and 5 of 1-O-methyl-2-deoxi-L-ribofuranoside of formula (V) by reaction with the suitable acyl chloride according to the desired product, having formula R'COCl in which R'CO is R.

The preferred amount of acyl chloride ranges between 2 and 5 moles of acyl chloride compared to the substrate of formula (V) to be acylated. Such reaction is carried out in presence of a tertiary amine base, preferably triethylamine, using as reaction solvent an aprotic solvent such as acetone, acetonitrile, toluene, mehylene chloride, tetrahydrofurane, or dimethylformamide. Preferably the reaction solvent is toluene.

According to a particular embodiment of the invention, the acylation reaction in step iv) is carried out at a temperature ranging between 0° C. and the boiling temperature of the solvent used.

The chlorination reaction of 1-methyl-3,5-di-O-acyl-2-deoxy-L-ribofuranoside (VI) is typically carried out by using as the solvent, a solvent from which the final product can be directly crystallised, selected for example from the group consisting of toluene, xylene, isopropyl ether, ethyl ether, chloro benzene and trichloroethane, preferably toluene.

The gaseous hydrochloric acid in step v) of the present process is preferably insufflated directly into the reaction mixture in presence of acetyl chloride that consumes methanol, which is a by-product of reaction, turning it into methyl acetate.

During bubbling of gaseous hydrochloric acid the temperature of reaction mixture has to be kept below 20° C., preferably below 15° C.

The obtained solid has to be vacuum exsiccated at a temperature preferably not higher than 40° C. in order to avoid its degradation.

The present invention also provides with a process for the preparation of 1-chloro-3,5-di-O-acyl-2-deoxy-L-ribofuranoside derivatives of formula (I) starting from 1-O-methyl-2-deoxy-L-ribofuranoside of formula (V) prepared according to the procedures known in the prior art, in two steps iv) and v) for which the considerations made above in relation to steps iv) and v) are respectively valid. The following examples are reported for illustrative and not limiting purpose of the invention.

EXAMPLE 1

Synthesis of 1-methyl-2-deoxy-D-ualactofuranoside [Compound of formula (III)] 100 g [mg] (0.6 mol) of 2-deoxy-D-galactose are suspended in 600 ml of anhydrous methanol. The suspension is cooled down to the inner temperature of 0° C., thereafter 4.5 ml (0.06 mol) of acetyl chloride are added slowly in order to control exothermy and keep the inner temperature below 3° C. 1 hour after the end of the addition, a solution is obtained. The reaction mixture is then kept under stirring at the temperature of 0-2° C. for a total of 2 hours and 30 minutes calculated from the end of addition of acetyl chloride. Then the reaction mixture is neutralized with 14.3 ml (0.06 mol) of a 25% solution of sodium methoxide in methanol. Methanol is eliminated through concentration with Rotavapor®, thus obtaining 115 g of a syrup containing about 103 g (0.58 mol) of 1-O-methyl-2-deoxy-D-galactofuranoside (yield =97%).

$^{13}$C-NMR (DMSO, 300 MHz): δ ppm 104,68 and 104,53 (C-1β and C-1α); 86,36 and 84,42 (C-4α and C-4β); 72.30, 71.28, 70.63, 70.45 (C-3α and β and C-5α and β); 63.34 and 63.26 (C-6β and C-6α); 54.56 and 54.51 (OCH$_3$α and β); 41.59 and 41.46 (C-2α and β).

EXAMPLE 2

Synthesis of 1-methyl-2-deoxy-5-aldehyde-L-ribo-pentadialdo-1,4-furanoside [Compound of Formula (IV)]

115 g of syrup of 1-O-methyl-2-deoxy-D-galactofuranoside (0.58 mol) prepared as described above in Example 1, are dissolved in 100 ml of water. The solution is externally cooled with a brine bath so that the inner temperature is below 0° C., thereafter 330 g of ice and, under strong stirring, 129 g (0.6 mol) of NaIO$_4$ are added to the reaction mixture After about 5 minutes a strong exothermy occurs, that is controlled by adding further 100 g of ice to the reaction mixture. The inner temperature has to be kept below 10° C.

After 30 minutes the reaction was checked by TLC. The salts are filtered out, and to the aqueous solution 4.5 g (0.03 mol) of calcium chloride dihydrate are added; the value of pH of the so obtained suspension is brought to 7-7.5 by adding about 3.3 g (0.04 mol) of calcium hydroxide.

The salts are vacuum filtered and washed with water. The aqueous phase is extracted with dichloromethane (130 ml). The aqueous solution is used directly in the following reaction. The yield of this reaction is considered as quantitative.

EXAMPLE 3

Synthesis of 1-methyl-2-deoxo-L-ribofuranoside [Compound of Formula (V)]

The aqueous solution of 1-O-methyl-2-deoxy-5-aldehydo-L-ribopentadialdo-1,4-furanoside, obtained in Examples 2, is cooled to 0° C., thereafter a solution is dropped into, prepared dissolving 9.4 g (0.25 mol) of NaBH$_4$ in 100 ml of water basificated at 10 pH with NaOH 30%.

During the addition, exothermy occurs, afterwards the addition is performed slowly so as to keep the inner temperature always below 15° C. At the end of the addition the reaction mixture is left under cool stirring for 30 minutes, thereafter a check is performed through TLC. The reaction mixture is neutralised by adding hydrochloric acid at 32% until pH=7. The solution is concentrated with a Rotavapor® till a syrup is obtained, afterwards the residue is dissolved with 120 ml of hot acetone. The suspension is warmed up to reflux and maintained at this temperature for 20 minutes.

In this way the dissolution of the syrup is achieved and the formation of a crystalline precipitate is obtained. The suspension is cooled down to 30° C. and then the precipitated salts are filtered out. The filtrated solution is concentrated to syrup, the re-dissolved twice with 120 ml of methanol and twice with 120 ml of toluene (each solvent rate is removed under vacuum before adding the following rate).

In this way the anhydrous syrup is obtained to be used directly in the subsequent reaction. 84 g of syrup are obtained containing 66.6 g (0.45 mol) of 1-O-methyl-2-deoxy-L-ribofuranoside as resulted from HPLC analysis (yield=77.5%).

$^{13}$C-NMR (DMS, 300 MHz): δ ppm 105.30 and 105.05 (C-1α and C-1β); 87.11 and 85.72 (C-4α and C-4β); 71.57 and 70.91 (C-3α and C-3β); 63.75 and 62.05 (C-5α and C-5β); 55.11 and 55.03 (OCH$_3$β and α); 41.42 and 41.33 (C-2α and C-2β).

EXAMPLE 4

Synthesis of 1-O-methyl-3,5-di-O-toluoyl-2-deoxy-L-ribofuranoside [Compound of Formula (VI) in which R is 4-methyl-benzoyl]

84 g of syrup (0.45 mol of 1-O-methyl-2-deoxy-L-ribofuranoside), prepared as described above in Example 3, are suspended in 470 ml of toluene and 205 ml (1.47 mol) of triethylamine. The suspension is warmed up to 40° C. under stirring, then 173 ml (1.3 mol) of toluoyl chloride are slowly dropped, and the temperature spontaneously raises to 60° C. After the addition, the suspension is kept under stirring at 60° C. for 5 hours, and thereafter an HPLC check is performed to evaluate the absence of the peak corresponding to the mono-substituted product. With a positive analytical check, the mixture is cooled to room temperature and 60 ml (0.54 mol) of N-methyl-piperazine are dropped into.

1 liter of water is added, then NaOH 30% is added until pH=9.0 and the phases are separated. To the toluenic phase 1 liter of fresh water is added and the solution is brought to pH=1.0 by dripping an aqueous solution of HCl 30%. The phases are separated, and the toluenic phase is dehydrated on anhydrous Na$_2$SO$_4$ for 1 hour, then the solid is filtrated.

Before proceeding, a HPLC check and a KF check are carried out. In the toluenic solution 154 g (0.40 mol) of 1-O-methyl-3,5-di-O-toluoyl-2-deoxy-L-ribofuranoside are found through HPLC analysis.

Yield=89%. $^{13}$C-NMR (CDCl$_3$, 300 MHz): δ ppm 105.69 and 105.14 (C-1α and C-1β); 81.99 and 81.04 (C-4α and C-4β); 75.50 and 74.70 (C-3α and C-3β); 65.22 and 64.39 (C-5α and C-5β); 55.15 (2 OCH$_3$); 39.37 and 39.34 (C-2α and C-2β).

EXAMPLE 5

Synthesis of 1-O-methyl-3.5-di-O-p-chloro-benzoyl-2-deoxy-L-ribofuranoside [Compound of Formula (I) in which R is 4-chloro-benzoyl]

The 1-O-methyl-3,5-di-O-p-chloro-benzoyl-2-deoxy-L-ribofuranoside is prepared with the same procedure as described above in Example 4 for the synthesis of 1-O-methyl-3,5-toluoyl-2-deoxy-L-ribofuranoside, using the same quantities of toluene and triethylamine and dripping into the reaction mixture 165 ml (1.3 mol) of p-chloro-benzoyl chloride.

In the final toluenic solution 166 g (0.39 mol) of 1-O-methyl-3,5-di-O-p-chloro-benzoyl-2-deoxy-L-ribofuranoside are measured by HPLC. Yield=86.6%.

$^{13}$C-NMR (CDCl$_3$, 300 MHz): δ ppm 105.11 and 104.25 (C-1α and C-1β); 82.12 and 81.23 (C-4α and C-4β); 76.55 and 75.51 (C-3α and C-3β); 66.01 and 65.12 (C-5α and C-5β); 39.66 (C-2).

EXAMPLE 6

Synthesis of 1-chloro-3,5-di-O-toluoyl-2-deoxy-L-ribofuranoside [Compound of Formula (I) in which R is 4-methyl-benzoyl]

To the toluenic solution of 1-O-methyl-3,5-di-O-toluoyl-2-deoxy-L-ribofuranoside, prepared as described above in Example 4, 77 ml (1.08 mol) of acetyl chloride are added. The solution is cooled down to 5° C. and hydrochloric acid is bubbled into the solution, controlling the bubbling so as to maintain the inner temperature below 15° C. After the addition the solution is left under stirring at 5° C., after about 30 minutes the product precipitates as white solid. After 1 hour a TLC check is performed in order to evaluate absence of the spot corresponding to the starting product.

With a positive analytical check the operation is proceeded forward, otherwise the suspension is left under stirring for a further hour. The apparatus is put under vacuum for 2 hours to remove gaseous hydrochloric acid in excess, then the solid is filtrated and washed with 100 ml of toluene and with 50 ml of hexane. The solid is exsiccated under vacuum at 35-40° C. until constant weight. 140 g (0.36 moles) of 1-chloro-3,5-di-O-toluoyl-2-deoxy-L-ribofuranoside are obtained. Yield=90%.

$^1$H-NMR (CDCl$_3$, 300 MHz): δ ppm 8-7.89 (4H, dd, aromatic); 7.28-7.22 (4H, dd, aromatic); 6.48 (1H, d, H-1); 5.57 (1H, ddd, H-3); 4.87 (1H, ddd, H-4); 4.64 (2H, AB system, CH$_2$-5); 2.81 (2H, m, CH$_2$-2).

$^{13}$C-NMR (CDCl$_3$, 300 MHz): δ ppm 166.63 and 166.39 (2 C=O); 144.51-126.91 (C aromatic); 95.56 (C-1); 84.93 (C-4); 73.77 (C-3); 63.72 (C-5); 44.75 (C-2); 21.95 and 21.91 (2 CH$_3$).

EXAMPLE 7

Synthesis of 1-chloro-3,5-di-O-p-chloro-benzoyl-deoxy-L-ribofuranoside [Compound of Formula (I) in which R is 4-chloro-benzoyl]

1-chloro-3,5-di-O-p-chloro-benzoyl-2-deoxy-L-ribofuranoside is prepared with the same procedure as that described above in Example 6 for the preparation of 1-chloro-3,5-di-O-toluoyl-2-deoxy-L-ribofuranoside.

151 g (0.35 mol) of 1-chloro-3,5-di-O-p-Cl-benzoyl-2-deoxy-L-ribofuranoside are obtained. Yield=89.7%.

$^1$H-NMR (CDCl$_3$, 300 MHz): δ ppm 8.05-7.40 (8H, m, aromatic); 6.48 (1H, d, H-1); 5.54 (1H, m, H-3); 4.84 (1H, m, H-4); 4.64 (2H, m, CH$_2$-5); 2.82 (2H, m, CH$_2$-2).

$^{13}$C-NMR (CDCl$_3$, 300 MHz): δ ppm 165.62 and 165.389 (2C=O); 140.61-128-23 (C aromatic); 95.57 (C-1); 84.94 (C-4); 74.35 (C-3); 64.25 (C-5); 44.86 (C-2).

What is claimed is:

1. Process for the preparation of 1-chloro-3,5-di-O-acyl-deoxy-L-ribofuranosidic derivatives of formula (I)

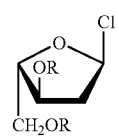
(I)

wherein R is an acyl group R'CO, in which R' is selected from the group consisting of alkyl groups C1-C6 and aryl groups C7-C13, possibly substituted with one or more substituents;

said process comprising the following steps:

i) reaction of 2-deoxy-D-galactose of formula (II) with methanol in the presence of an acid as catalyst to obtain the 1-O-methyl-2-deoxy-D-galactofuranoside of formula (III):

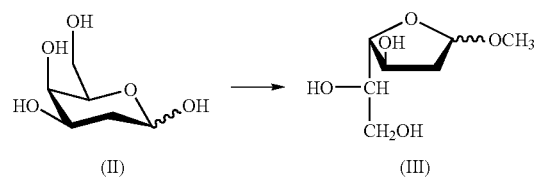

ii) oxidation of 1-O-methyl-2-deoxy-D-galactofuranoside of formula (III) coming from step i) with sodium meta periodate to obtain the corresponding aldehyde of formula (IV):

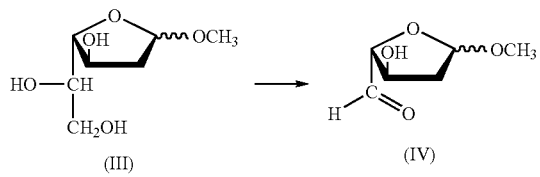

iii) reduction of the aldehyde of formula (IV) coming from step ii) with sodium borohydride to obtain the 1-O-methyl-2-deoxy-L-ribofuranoside of formula (V):

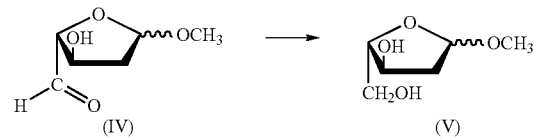

iv) acylation of O-methyl-2-deoxy-L-ribofuranose of formula (V) coming from step iii) with an acyl chloride of formula R'COCl, in presence of a tertiary amine base in an aprotic solvent to obtain the corresponding 1-O-methyl-3,5-di-O-acyl-2-deoxy-L-ribofuranoside having formula (VI):

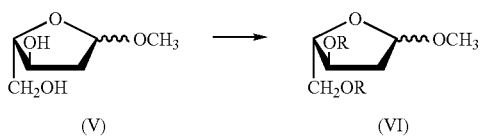

in which R' and R are defined as above;

v) chlorination of 1-O-methyl-3,5-di-O-acyl-2-deoxy-L-ribofuranoside of formula (VI) coming from step iv) with gaseous hydrochloric acid at a temperature lower than 20° C. to obtain 1-chloro-3,5-di-O-acyl-2-deoxy-L-ribofuranoside of formula (I):

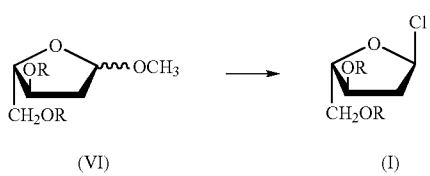

where R is defined as above.

2. Process according to claim 1, wherein said

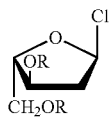

substituents are selected from the group consisting of halogens, alkyl groups C1-C4, alkyloxy groups C1-C4 and nitro groups.

3. Process according to claim 1, wherein R' is benzoyl.

4. Process according to claim 3, wherein R' is selected from between p-toluoyl and p-chloro-benzoyl.

5. Process according to claim 1, wherein the amount of acyl chloride in step iv) ranges between 2 and 5 moles per mole of the amount of 1-methyl-2-deoxy-L-ribofuranoside of formula (V).

6. Process according to claim 1, wherein said tertiary amine base in step iv) is triethylamine.

7. Process according to claim 1, wherein said aprotic solvent in step iv) is selected from the group consisting of acetone, acetonitrile, toluene, methylene chloride, tetrahydrofuran, and dimethylformamide.

8. Process according to claim 7, wherein said aprotic solvent is toluene.

9. Process according to claim 1, wherein said acylation reaction in step iv) is carried out at a temperature ranging between 0° C. and the boiling point of the solvent used.

10. Process according to claim 9, wherein said acylation reaction in step iv) is carried out at a temperature of 60° C.

11. Process according to claim 1, wherein said chlorination reaction in step v) is carried out by insufflating gaseous hydrochloric acid in the reaction mixture in presence of acetyl chloride.

12. Process according to claim 1, wherein said chlorination reaction in step v) is carried out at a temperature below 15° C.

13. Process according to claim 1, wherein said chlorination reaction in step v) is carried out in a solvent selected from the group consisting of toluene, xylene, isopropyl ether, ethyl ether, chloro-benzene and trichloroethane.

14. Process according to claim 13, wherein said solvent is toluene.

15. Process according to claim 1, wherein said reaction at step i) is carried out with anhydrous methanol in amount ranging between 2 and 20 litres per-kilogram of 2-deoxy-galactose of formula (II).

16. Process according to claim 1, wherein in step i) said acid catalyst is obtained in situ by hydrolysis of the corresponding acyl chloride.

17. Process according to claim 16, wherein said acid catalyst is obtained in situ by hydrolysis of acetyl chloride.

18. Process according to claim 1, wherein said reaction in step i) is carried out maintaining the inner temperature of reaction below 3° C.

19. Process according to claim 1, wherein said reaction in step ii) is carried out using from 1 to 1.5 moles of sodium metaperiodate per mole of the compound of formula (III).

20. Process according to claim 1, wherein said reaction in step ii) is carried out at a temperature below 10° C.

21. Process according to claim 1, wherein said reaction in step iii) is carried out in water using from ⅓ to 1 moles of sodium borohydride per mole of the compound of formula (IV).

22. Process according to claim 1, wherein said reaction in step ii) is carried out at a temperature below 15° C.

* * * * *